United States Patent [19]

Mathews III et al.

[11] Patent Number: 4,841,087
[45] Date of Patent: Jun. 20, 1989

[54] ACRYLONITRILE DIMERIZATION PROCESS

[75] Inventors: Marion J. Mathews III; P. Robert Peoples, both of Pensacola, Fla.

[73] Assignee: Monsanto Company, St. Louis, Mo.

[21] Appl. No.: 169,069

[22] Filed: Mar. 14, 1988

Related U.S. Application Data

[63] Continuation of Ser. No. 39,247, Apr. 17, 1987, abandoned.

[51] Int. Cl.$^4$ ............................................. C07C 121/20
[52] U.S. Cl. ....................................................... 558/363
[58] Field of Search .......................................... 558/363

[56] References Cited

U.S. PATENT DOCUMENTS 4,102,915  7/1978  Jennings et al. .................... 558/363
4,126,632  11/1978  Hogan et al. ........................ 558/363
4,138,428  2/1979  Jennings et al. .................... 558/363
4,639,538  1/1987  Hovey et al. ........................ 558/363

OTHER PUBLICATIONS

Negishi, et al., J. A. C. S., 100 (1978), pp. 2254–2256.
Tameo, et al., J. A. C. S., 94 (1972), pp. 4374–4376; 9268–9269.
J. A. C. S., 101 (1979) pp. 4406–4407, (Author unknown).
Rathke et al., J. A. C. S., 100 (1978), pp. 3623–3625.
Hendriksen et al., J. A. C. S., 98 (1976), pp. 4662–4664.

*Primary Examiner*—Joseph P. Brust
*Attorney, Agent, or Firm*—Thomas N. Wallin

[57] ABSTRACT

Acrylonitrile dimerization is improved by increasing the proportions of catalyst used in the reaction mixture.

5 Claims, No Drawings

ACRYLONITRILE DIMERIZATION PROCESS

This is a continuation of application Ser. No. 039,247, filed Apr. 17, 1987 and now abandoned.

BACKGROUND OF THE INVENTION

This invention relates to an improved process for dimerization of acrylonitrile to predominantly straight-chain $C_6$ dinitriles such as 1,4-dicyanobutene. More particularly, the invention relates to improvements in dimerization processes using organic phosphinite and/or phosphonite catalysts in the presence of a proton-donating solvent.

Dimerization of acrylonitrile to yield 1,4-dicyanobutenes by using organic phosphinite or phosphonite catalyst in thee presence of a proton-donating solvent is described, for example, in U.S. Pat. Nos. 4,126,632; 4,102,915; and 4,138,428, the disclosures of said patents being incorporated herein by reference. According to the teachings of these patents the acrylonitrile is contacted wiith an organic phosphorus (III) compound which has at least one hydrocarbyl and at least one alkoxy or cycloalkoxy group attached to the phosphorus atom or atoms, the acrylonitrile being dissolved in an organic solvent capable of donating protons and the acrylonitrile and solvent being substantially dry.

Suitable organic phosphorus (III) compounds include those of the formulae:

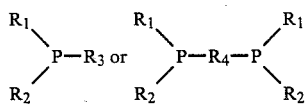

where $R_1$ is a hydrocarbyl group, $R_2$ is an alkoxy or cycloalkoxy group, $R_3$ is hydrocarbyl, alkoxy or cycloalkoxy group or other monovalent radical, and $R_4$ is a divalent hydrocarbyl, hydrocarbyloxy or other disfunctional group. It is also possible that one or more groups $R_1$ to $R_3$ may form part of one or more ring systems.

The hydrocarbyl groups may be aryl, alkyl, aklylaryl (polycyclic) or cycloalkyl.

The reaction is conducted in the presence of an organic solvent since in the absence of solvent rapid polymerization of the acrylonitrile occurs. Suitable solvents are proton donating solvents which are substantially unreactive in respect of addition to, or reaction with, the unsaturated linkage of the acrylonitrile or the products of acrylonitrile dimerization. Furthermore, the solvent must not react with the phosphorus compounds or catalytic intermediates to form inactive phosphorus species at such a rate as to seriously impair the dimerization reaction. For example, phenols have been found to be unsuitable in this respect.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

It is further taught that in order to reduce the amount of hexamer and/or other oligomers or polymers (hereafter referred collectively as polymeric by-products or merely polymers) which may be co-produced with the desired dimeric products, it is often desirable to add an inert, non-hydroxylic co-solvent to the reaction mixture used in the process. The co-solvent is dried to a level which maintains the overall anhydrous state of the system.

Suitable non-hydroxylic organic co-solvents include hydrocarbons, for example, hexane, cyclohexane, toluene, and petroleum ethers; ethers, for example, tetrahydrofuran, diethyl ether and diisopropyl ether; and nitriles, for example, acetonitrile, propionitrile; and fluorobenzenes. The hydrocarbon co-solvents are generally preferred. To avoid ambituity, inert non-hydroxylic co-solvents such as described will, hereafter, be consistantly referred to as "co-solvents" to clearly distinguish them from proton donating solvents employed in the reaction mix.

The reaction is conducted in the substantial absence of water.

With respect to proportions of ingredients in the reaction mixture, the referenced patents disclose 0.01 to 5% by volume of the phosphorus compound and a 1:40 to 40:1 ratio of proton-donating solvent to co-solvent.

SUMMARY OF THE INVENTION

It has now been found that if reactions of the type described are conducted with substantially increased amounts of catalysts containing high proportions of aryl moieties, significant improvements in reaction rate without undue loss of selectivity or increased by product formation is obtained. Moreover, co-solvent usage can be reduced or eliminated without experiencing by-product formation problems discussed in the referenced patent. This, of course, facilitates product separation and minimizes material handling problems sometimes associated with use of co-solvents. In addition, this invention results in a very significant increase in product space-time yields (which makes use of substantially smaller reactoers practical).

DESCRIPTION OF THE PREFERRED EMBODIMENTS

In accordance with the present invention, the dimerization catalyst utilized is a represented by the formula:

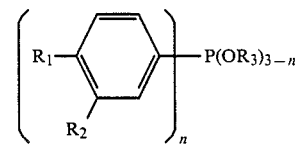

wherein n is 1 or 2, $R_1$ and $R_2$ may be the same or different and may be hydrogen; an alkyl group such as methyl, ethyl, etc.; cycloalkyl groups; aryl groups; or heteroatom containing substituents such as N,N-dialkyl, O-alkyl, trifluoromethyl, cyano, etc. $R_3$ may be alkyl, cycloalkyl or aryl. Preferably, $R_1$ and $R_2$ are hydrogen or methyl and $R_3$ is isopropyl. The aryl moieties (exclusive of substituents thereon) will constitute at least 25% by weight of the catalyst. A preferred catalyst within the scope of the formula is isopropyldiphenylphosphinite.

In the dimerization process, the catalyst will constitute from 16% to 90% by weight of the reaction mixture with amounts of from 30 to 90% being preferred. The use of at least 70% catalyst is most preferred particularly when no co-solvent is present. In most instances it is preferred that no inert co-solvent be utilized. However, use of a co-solvent may be desired if lower proportions of catalyst in the range specified are utilized. In such case the volume of catalyst should be at least 28% of the volume of the co-solvent.

Aside from the foregoing critical factors, the dimerization reaction will be conducted as taught in the earlier referenced U.S. Patents.

As previously mentioned, the reaction is conducted in the presence of a proton donating solvent. Suitable solvents are substantially unreactive in respect of addition to, or reaction with, the unsaturated linkage of the acrylonitrile or the products of acrylonitrile dimerization. Furthermore, the solvent must not react with the phosphorus compounds or catalytic intermediates to form inactive phosphorus species as such a rate as to seriously impair the dimerization reaction. For example, phenols have been found to be unsuitable in this respect.

Preferably hydroxylic solvents such as alcohols, are used provided that they do not react adversely with acrylonitrile, the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range of 5 to 20% by volume, calculated on the total volume of the reactants, but the optimum concentration will vary with the precise nature of the solvent and the catalyst compound. The reaction is conducted in the substantial absence of water.

Particularly when larger amounts of catalyst are utilized, the use of inert, non-hydroxylic co-solvents is neither necessary or desirable. However, in some instances such co-solvents may be employed as previously discussed. Suitable non-hydroxylic organic solvents include hydrocarbons such as hexane, cyclohexane, benzene, toluene, and petroleum ethers; ethers, e.g., terahydrofuran, diethyl ether, diisopropyl ether; nitriles, e.g., acetonitrile, propionitrile; and fluorobenzenes. If any co-solvent is used, aromatic co-solvents are preferred.

As previously noted, the reaction is conducted in the absence of water. Thus, the acrylonitrile, proton-donating solvent and co-solvent, if employed, must be dried before use, otherwise the reaction may be completely inhibited. In particular, acrylontrile, which commonly contains as much as 4000 ppm of water, even after distillation, must be rigorously dried. It is also preferrable that hydroquinone stabilizers, which are present in acrylonitrile as supplied be removed. Any suitable drying technique may be used, provided that the final water level is sufficiently low, for example, acrylonitrile and hodryxylic solvents may be dried by being contracted with calcium hydride or a 3A or 4A molecular sieve. Azeotropic distillation may be employed.

The concentration of acrylonitrile in the solvent or solvent mixture generally should range from 5 to 75% by volume. The concentration of acrylonitrile is kept as high as possible in order to optimize throughput while maintaining useful yields and thus concentrations in the range of 5 to 20% by volume are generally preferred.

The reaction temperature is commonly in the range 0° to 120° C.; but it is generally preferred to keep the temperature below 75° C. to minimize polymerization of the acrylonitrile and dimeric products. Preferably, the reaction temperature is in the range 20° to 70° C. It is noted that the reaction will proceed below 0° C., maintaining selectivity, but at a reduced rate.

The reaction may be carried out batchwise or continuously.

The dimeric products of the reaction are predominantly linear $C_6$ dinitriles, especially the 1,4-dicyanobutenes. Dimer selectivities greater than 90 wt % (calculated on total dimeric product) may be readily obtained and selectivities as high as 98% are obtainable. Actual yields are generally in the 85–95% range.

The desired products may be readily separated from the reaction mixture for example by fractional distillation or solvent extraction.

EXAMPLE 1

Acrylonitrile is dimerized to 1,4-dicyanobutene using isopropyl diphenylphosphinite catalyst. Isopropyl alcohol is used as the proton-donating solvent. Reaction mix proportions, reaction conditions and results are shown in Table 1 below.

TABLE 1

| Run Number | 1 | 2 | 3 | 4 | 5 | 6 | 7 |
|---|---|---|---|---|---|---|---|
| Feed Comp., wt % | | | | | | | |
| Acrylonitrile | 20.5 | 20.4 | 20.4 | 20.4 | 17.2 | 9.66 | 19.5 |
| Isopropyl Alcohol | 6.6 | 6.6 | 6.6 | 6.6 | 5.6 | 5.0 | 6.4 |
| Benzene | 56.9 | 40.8 | 10.0 | 0 | 61.6 | — | 70.0 |
| Catalyst | 16.0 | 32.2 | 63.0 | 73.0 | 15.7 | 85.1 | 4.0 |
| Reactor Temp., °C. | 40 | 40 | 40 | 40 | 40 | 40 | 40 |
| Residence Time, hr. | 2.0 | 1.0 | 0.7 | 0.5 | 2 | 0.25 | 7 |
| Product Comp., wt % | | | | | | | |
| Acrylonitrile | 6.7 | 4.8 | 1.6 | 1.5 | 7.3 | 4.47 | 9.5 |
| cis-1,4-dicyanobutene-1 | 7.68 | 8.23 | 9.27 | 9.16 | 5.73 | 2.92 | 5.86 |
| trans-1,4-dicyanobutene-1 | 4.71 | 5.17 | 6.20 | 6.15 | 3.48 | 1.85 | 3.27 |
| Methyleneglutaronitrile | 0.57 | 0.61 | 0.73 | 0.77 | 0.40 | 0.213 | 0.41 |
| Solids | 0.12 | 0.16 | 0.34 | 0.41 | 0.007 | .001 | 0.019 |
| % AN Conversion | 67 | 76 | 92 | 93 | 57 | 54 | 51 |
| Product Yield, % | | | | | | | |
| 1,4-dicyanobutene-1 | 89.8 | 85.9 | 82.3 | 81.0 | 92.8 | 91.9 | 91.3 |
| Methyleneglutaronitrile | 4.1 | 3.9 | 3.9 | 4.1 | 4.0 | 4.1 | 4.1 |
| Unidentified | 5.2 | 9.2 | 12.0 | 12.7 | 3.1 | 4.0 | 4.4 |
| Solids | 0.9 | 1.0 | 1.8 | 2.2 | 0.1 | 0.23 | 0.2 |

TABLE 1-continued

| Run Number | 1 | 2 | 3 | 4 | 5 | 6 | 7 |
|---|---|---|---|---|---|---|---|
| *$k_2 \times 10^4$ | 2.8 | 3.3 | 3.7 | 4.6 | 2.1 | 2.5 | 1.4 |

*$k_2$ = rate of reaction of AN expressed as liters per mole per second.

EXAMPLE 2

Diisopropyl phenylphosphonite (DIPPP) was tested as a catalyst for AN dimerization without cosolvent. Results are shown in Table 2, below.

TABLE 2

| Feed Comp, % | % by Weight | % by Weight |
|---|---|---|
| Acrylonitrile | 19.8 | 10.4 |
| Isopropyl Alcohol | 4.8 | 5.3 |
| Catalyst | 75.4 | 84.3 |
| Hold at 40° C. for 60 min. | | |
| Results: | | |
| % AN conv. | 100 | 100 |
| DCB Yield, % | 46 | 56 |

As seen from the table AN dimerization was catalyzed by DIPPP at substantial rates. It is believed that further optimization (lower temperature, shorter reaction time, different IPA concentration) would lead to substantially higher yields.

We claim:

1. In a process for dimerizing acrylonitrile to obtain 1,4-dicyanobutenes, said process comprising dissolving acrylonitrile in an organic solvent capable of donating protons but substantially unreactive with respect to acrylonitrile and organic phosphorus (III) compounds; contacting the acrylonitrile with an organic phosphorus (III) catalyst compound at a temperature from 0° to 120° C. under substantially anhydrous conditions; the improvement characterized in that:

(a) the catalyst is represented by the formula:

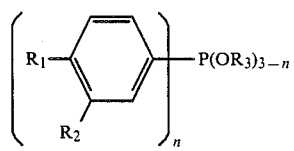

wherein n is 1 or 2; $R_1$ and $R_2$ are each hydrogen, alkyl, aryl, cycloalkyl or heteroatom containing substituents; $R_3$ is alkyl, cycloalky or aryl; and aryl moieties constitute at least 25% by weight of the catalyst (b) the catalyst constitutes 16% to 90% by weight of the reaction mixture and at least 28% of the volume of any co-solvent present, and (c) the rate constant is higher than obtained with an otherwise identical reaction mixture containing less than 16% by weight catalyst under identical conditions.

2. The process of claim 1 where no cosolvent is present.

3. The process of claim 1 wherein the catalyst constitutes 30% to 90% by weight of the reaction mixture.

4. The process of claim 2 wherein the catalyst constitutes at least 70% by weight of the reaction mixture.

5. The process of claim 1 wherein the catalyst is isopropyl diphenylphosphonite.

* * * * *